(12) United States Patent
Korten et al.

(10) Patent No.: US 10,182,892 B2
(45) Date of Patent: Jan. 22, 2019

(54) METHOD AND SYSTEM OF MAKING A CUSTOMIZED DENTAL BLANK

(71) Applicant: 3M INNOVATIVE PROPERTIES COMPANY, St. Paul, MN (US)

(72) Inventors: Malte Korten, Moorenweis (DE); Helmar Mayr, Kaufering (DE); Michael Jahns, Gilching (DE)

(73) Assignee: 3M Innovative Properties Company, St. Paul, MN (US)

( * ) Notice: Subject to any disclaimer, the term of this patent is extended or adjusted under 35 U.S.C. 154(b) by 500 days.

(21) Appl. No.: 14/404,038

(22) PCT Filed: May 29, 2013

(86) PCT No.: PCT/US2013/043131
§ 371 (c)(1),
(2) Date: Nov. 26, 2014

(87) PCT Pub. No.: WO2013/181262
PCT Pub. Date: Dec. 5, 2013

(65) Prior Publication Data
US 2015/0335407 A1    Nov. 26, 2015

(30) Foreign Application Priority Data
Jun. 1, 2012 (EP) .................................... 12170470

(51) Int. Cl.
*A61C 13/08* (2006.01)
*A61C 13/083* (2006.01)
(Continued)

(52) U.S. Cl.
CPC ...... *A61C 13/0022* (2013.01); *A61C 13/0004* (2013.01); *A61C 13/0013* (2013.01);
(Continued)

(58) Field of Classification Search
CPC .............. A61C 13/0004; A61C 13/083; A61C 13/0013; A61C 13/0022; A61C 13/082; A61C 13/09; B29C 67/0081
See application file for complete search history.

(56) References Cited

U.S. PATENT DOCUMENTS

| 4,684,862 A | 8/1987 | Rohrle |
| 5,151,044 A | 9/1992 | Rotsaert |

(Continued)

FOREIGN PATENT DOCUMENTS

| DE | 19944130 | 4/2001 |
| DE | 102007036370 | 10/2008 |

(Continued)

OTHER PUBLICATIONS

International Search Report for PCT International Application No. PCT/US2013/043131, dated Aug. 27, 2013, 4pgs.

(Continued)

*Primary Examiner* — Robert J Grun (57) ABSTRACT

A method of making a customized dental blank comprises the steps of providing individual tooth color information, forming an open-celled dental blank precursor, providing the open-celled dental blank precursor with color in accordance with the individual tooth color information, and compressing the dental blank precursor. The method helps maximizing the optical quality of dental restoration at minimized costs.

14 Claims, 3 Drawing Sheets

(51) Int. Cl.
*A61C 13/00* (2006.01)
*A61C 13/09* (2006.01)
*B29C 64/165* (2017.01)

(52) U.S. Cl.
CPC .......... *A61C 13/082* (2013.01); *A61C 13/083* (2013.01); *A61C 13/09* (2013.01); *B29C 64/165* (2017.08)

(56) References Cited

U.S. PATENT DOCUMENTS

| | | |
|---|---|---|
| 6,238,601 B1 | 5/2001 | Salomonson |
| 9,456,884 B2 | 10/2016 | Uckelmann |
| 2006/0025135 A1 | 2/2006 | Karaoguz |
| 2007/0126157 A1 | 6/2007 | Bredt |
| 2007/0292597 A1 | 12/2007 | Ritzenberger |
| 2010/0212584 A1 | 8/2010 | Ederer |
| 2011/0190446 A1 | 8/2011 | Matsui |
| 2011/0275031 A1* | 11/2011 | Jana ................. A61C 13/0022 433/172 |
| 2012/0052186 A1 | 3/2012 | Junglas |

FOREIGN PATENT DOCUMENTS

| | | |
|---|---|---|
| EP | 1486476 | 12/2004 |
| EP | 2363270 | 9/2011 |
| JP | 2004-035332 | 2/2004 |
| JP | 2012-024395 | 2/2012 |
| RU | 2057492 | 12/1993 |
| WO | WO 2002-09612 | 2/2002 |
| WO | WO 2008-083358 | 7/2008 |
| WO | WO 2012-078533 | 6/2012 |
| WO | WO 2013-095968 | 6/2013 |
| WO | WO 2014-179141 | 11/2014 |

OTHER PUBLICATIONS

1507 Extended EP Search Report for EP12170470.4, PCT/US2013/043131, dated Nov. 12, 2012, 6pgs.

* cited by examiner

METHOD AND SYSTEM OF MAKING A CUSTOMIZED DENTAL BLANK

FIELD OF THE INVENTION

The invention relates to a method of making a customized dental blank, and in particular a method in which an open-celled blank precursor is formed from particles according to individual tooth color information. The invention further relates to a system for making such customized blank, as well as to a customized dental blank.

BACKGROUND ART

In the field of dentistry, the restoration of a patient's tooth or teeth generally includes the replacement of the natural tooth substance by an artificial substance. For larger restorations, pre-finished dental restorations or prostheses are commonly used to replace the tooth or teeth or at least part of those.

Ceramic materials are widely used for making high-quality dental restorations because of their good physical, aesthetic and biological properties. These restorations are often manufactured in automated processes, which typically include at least one or more of the steps of:
digitally capturing the shape of a patient's teeth, for example by scanning a model of the teeth or the actual teeth in the patient's mouth;
making a design of the restoration using computer-aided design (CAD) software; and
manufacturing the restoration from the design using a Computer Numerical Controlled (CNC) machine.

In the manufacturing of dental restorations from ceramic materials various automated processes are established in practice. One common method includes the preparation of standardized blanks that subsequently can be used to machine individual dental restorations or precursors thereof by removing material from the blank. Except for providing such blank at a sufficient size suiting for a multiplicity of different types of dental restorations, the shape of the blank typically does not correlate with any individual shape of a tooth in patient's mouth.

While such processes provide various advantages meanwhile so-called build-up processes have been proposed for making dental restorations. Such a build-up process typically allows building up an individual dental restoration in substantially its desired individual shape, generally by subsequently adding material to create that shape instead of providing an oversized standardized blank from which material is removed in a subsequent process.

Copending international patent application PCT/US2011/063357 describes such a build-up process and corresponding devices for making a dental restoration. Although a precursor of the dental restoration obtained by the process described may be oversized such oversize is eliminated by sintering of the precursor without substantially changing the shape except for generally three-dimensionally shrinking the shape of the precursor. Accordingly in the described process the shape of the oversized dental restoration precursor correlates to the final shape of the final dental restoration.

Although existing processes for making dental restoration are advantageous in different respects there is a general desire to provide a process for making individual or customized dental restorations at a high degree of automation, maximized quality and minimized costs.

SUMMARY OF THE INVENTION

In one aspect the invention relates to a method of making a customized dental blank. Such a blank is preferably usable for making a dental restoration by material removal. Examples of dental restorations include one or more crowns, bridges, veneers, implants, abutments, root-pins, orthodontic brackets, dental support structures, inlays, onlays, full arch prostheses and parts thereof.

The method comprises the steps of:
providing individual tooth color information, for example tooth color information associated with one or more teeth of a patient;
forming an open-celled dental blank precursor from particles by an automated build-up technique;
providing the open-celled dental blank precursor with color in accordance with the individual tooth color information; and
compressing the open-celled dental blank precursor to form the dental blank.

The invention is advantageous in that it allows for providing a dental blank having a standardized outer shape but which is customized to meet color requirements related to an individual patient or an individual dental application. Further the invention allows for the use of established manufacturing technology which is based on material removal, but also to take advantage from build-up technology. Accordingly a maximized aesthetic dental restoration may be achieved without the need of entirely changing the manufacturing technology in the dental lab. The invention also allows for making several identical customized dental restorations or multiple different dental restorations for the same patient or multiple different restorations for different patients. The invention is also advantageous in that it preferably allows for making a final dental restoration out of a ceramic material without a veneer.

For the purpose of this invention a customized dental blank includes, but is not limited to, a blank which is customized in one or more respects but is standardized in at least one other respect. For example the customized dental blank may be customized in color, but standardized in shape.

For the purpose of this specification a "particle" means a substance being a solid having a shape which can be geometrically determined. The shape can be regular or irregular. Particles can typically be analyzed with respect to particle size and particle size distribution, for example.

In one embodiment the dental blank precursor is formed by a bulk of particles which on the one hand generally are in contact with each other but which on the other hand leave spaces between. In other words the particles may be present in the form of a powder. For the purpose of this specification a "powder" means a generally dry bulk composed of a large number of very fine particles that may flow freely when shaken or tilted. In particular such powder may be in the form of a generally loose accumulation of particles which generally do not adhere with each other, or eventually just slightly adhere with each other.

In one embodiment the method comprises the step of providing the particles with different colors in accordance with the individual tooth color information. The color may for example be added at predetermined spatial locations to generally uniformly colored or generally non-colored particles. Further the method may comprise the step of providing differently colored particles in accordance with the individual tooth color information. For example the differently colored particles may be deposited at a predetermined spatial arrangement relative to each other. Thus the open-celled dental blank may be provided with one or more colors in accordance with the individual tooth color information. The individual tooth color information is preferably determined in a step preceding the actual coloring. Accordingly the method may comprise the step of determining the individual tooth color information. The individual tooth color information may comprise at least one color in the form of color data, but preferably comprises at least a first color and a second color in the form of color data.

For the purpose of this specification "color data" are in a format which can be processed by a computer, and may contain information about color, translucency, reflectivity and/or brightness of a surface. Such surface may for example relate to a surface portion of a natural tooth or a dental restoration. Further the color data may represent or comprise a L*a*b* value and/or a color code as for example obtainable from the VITA 3D™ Master shade guide.

In particular the method may comprise the step of determining the first color and the second color. Further the method may comprise the step of creating a color gradient based on the first and second color.

The individual tooth color information, for example the first color and second color, may be determined manually, for example by a dental practitioner. The dental practitioner may for example determine the first and second color at a natural tooth in a patient's mouth. The dental practitioner may particularly determine the first and second color at a natural tooth in the vicinity of the tooth to be restored. This is because a dental restoration provided with colors similar to a tooth nearby typically matches optically pleasantly in the patient's dentition. One of the first and second color thereby may be determined in the vicinity of the occlusal end of a natural tooth. And the other one of the first and second color may be determined on the same tooth but in the vicinity of the gums. Other positions may be used as appropriate, which a dental practitioner will be able to determine. The first and second colors may be measured by a color measuring device which displays or transmits the colors in the form of color data. Such color data may be directly used in the individual tooth color information. However the color data may further be determined by manual comparison with a shade guide (for example the VITA 3D™ shade guide), or manual determination and measuring may be combined. In this case certain color codes of the shade guide may form the color data.

Typically a natural tooth exhibits a color gradient between different positions on the tooth. Such a gradient may be computer emulated in the step of creating a color gradient based on the first and second color. The gradient may be simply created by interpolation, for example linear interpolation, between the first and second colors. However the gradient may further be designed on a CAD system by a user. The first and second color and/or the gradient may however be further determined by color measuring and/or color scanning (for example capturing shape including corresponding colors at coordinates in that shape). The present invention is however not limited to the design of a color gradient although such a color gradient may be easily created based on only two colors. In other embodiments a user may for example manually define different colors for different portions in a three-dimensional of a virtual model, for example of a dental restoration or a dental blank as for example disclosed in co-pending European patent application 11195192.7 which is incorporated herein by reference.

In one embodiment the method comprises the step of providing the individual tooth color information with coordinates which are associated with the color data. For example the individual tooth color information may comprise a first coordinate associated with the first color and a second coordinate associated with the second color. Thus the positions of the first and second color may be represented within the individual tooth color information. Further the individual tooth color information may comprise a plurality of coordinates associated with colors of the color gradient (or any other spatial color pattern). Thus the color gradient may be represented by coordinates and corresponding color data at those coordinates.

In one embodiment the method comprises the step of assigning the dental blank with the individual tooth color information associated with a patient or a patient's tooth. This method step is preferably performed virtually on a computer system. In this step the individual tooth color information, determined as described before, is preferably used to determine the coloring of the dental blank. For assigning the blank with color information the shape of the blank and the individual tooth color information may be stored in a computer and combined by computer aid. The shape of the blank may be represented by a three-dimensional model of the blank, and the individual tooth color information may be virtually interrelated with the blank model. For example a first coordinate and a second coordinate of the blank model may be assigned the first and second color, respectively. In case the individual tooth color information comprises coordinates associated with the first and second color such coordinates may be used to determine the first and second coordinate in the blank model. In practice the first and second color, or further colors, may be represented in a coordinate system which may be virtually or visually superimposed with the coordinate system of the blank. In other words the colors determined at a patient's dentition may be virtually placed in the blank model in a true to scale or proportionally scaled fashion.

In one embodiment a virtual model of the dental blank is represented by a virtual partial model for each layer the blank is formed of, including color data representing the color of that layer. Such color data may further include two or more colors and a correlation between the colors and coordinates the colors are assigned to within the layer.

In one embodiment the steps of forming the dental blank precursor and providing the dental blank precursor with the color are performed in combination, for example in a shared sequence of repeatedly performed method steps. In particular the dental blank precursor may be formed by subsequently layering layers of particles on top of each other while each layer is provided with one or more particular color as appropriate to achieve the overall coloring of the dental blank precursor in accordance with the individual tooth color information. Thus based on the individual tooth color information the entire volume of the blank model may be assigned colors. The blank model may be colored according to a color gradient based on the first and second color, or otherwise as appropriate. Thereby the blank model may be assigned a multiplicity of layers stacked in a first dimension with each layer having an assigned color of the color gradient. Such layers preferably have a uniform thickness and extend in second and third dimensions to the boundaries of the blank shape. Thereby each layer preferably has a generally uniform thickness, and further a multiplicity of layers or all layers may have generally the same thickness. The entire volume of one layer may be assigned the same color or a two-dimensional pattern of different colors. Accordingly a build-up process for manufacturing the blank may reproduce such a layer with the assigned color(s). The blank model may further be assigned colored layers in two or all three dimensions whereby overlapping layers in different dimensions virtually superimpose. For example a layering in all three different dimensions results in virtual cubes of the blank model assigned with certain colors and layering in two-dimensions in virtual sticks of the blank model assigned with certain colors.

Accordingly the blank may be assigned such color gradient or pattern along one dimension only and may be uniformly colored along the other dimensions.

In one embodiment the assignment of the individual tooth color information to the blank is performed on a CAD system. Such a system may visualize the shape of a blank in which color information can be added, for example by a user. Although the CAD system may be further adapted to design and visualize also the shape of the dental restoration, for example within boundaries of the blank, the coloring of the blank is preferably independent from the shape of the dental restoration. In particular the colors assigned to the blank model are preferably not limited to boundaries defined by the shape of the dental restoration, but extend outside such boundaries, for example through the entire blank.

In one embodiment the method comprises the step of providing individual dental restoration shape information associated with the particular patient. The individual dental restoration shape information may be obtained by scanning at least part of the tooth to be restored. Further the individual dental restoration shape information may be obtained by design, for example using a dental CAD system. For the design an electronic library holding digital models of standard tooth shapes may be used. A selected tooth model may subsequently be modified by a user of the CAD system in accordance with the clinical situation in the patient's mouth. Such a dental CAD system is for example available under designation LAVA™ CAD/CAM System from 3M Deutschland GmbH, Germany.

In one embodiment the method comprises the step of providing the dental blank precursor and the dental blank obtained therefrom with a shape that is independent from the dental restoration shape. In a further embodiment the method comprises the step of determining the position of the dental restoration within the boundaries of the blank. Because a blank obtained by the method of the invention is colored independent from the shape of the dental restoration the dental restoration may be machined out of the blank at any desired position within the blank. Because the blank is colored according to individual tooth color information associated with a patient the resulting actual coloring of the dental restoration depends however on the position at which the restoration is machined out of the blank. Thus the positioning of the dental restoration within the blank may be used to control, within the limits provided by the coloring of the blank, the coloring of the final dental restoration. For example a more natural optical appearance of a dental restoration placed between natural teeth in a patient's mouth can be obtained through slight variations in color between the natural teeth and the restoration. Slight color deviations between two teeth placed directly side by side typically appear more natural than two identically colored neighboring teeth, for example. In particular in the preparation of multiple different dental restorations for placement directly side by side in a patient's mouth variations in color may be aesthetically advantageous. Such variations may be easily obtained by varying the position of the dental restoration relative to the blank.

The position of the dental restoration within the blank is preferably determined prior to machining the blank. On a computer, for example the CAD system mentioned above, a three-dimensional model of the dental restoration may be virtually positioned within the blank model at a desired position. For example translucent or transparent visualizations of the blank model and the dental restoration model may be visualized, and a user may drag the dental restoration model within the blank model (or vice versa) to a desired position. However the position of the dental restoration and the blank may further be automatically determined. For example the coordinates used for coloring of the blank may further be used to determine the coordinates of the dental restoration relative to the blank. To cause variations of the position a random generator may be used which provides tolerance data usable to offset the position within desired limits.

In one embodiment the particles comprise or essentially consist of ceramic material. The ceramic material preferably comprises or essentially consists of zirconia. The skilled person will recognize that glass ceramic materials may be used although zirconia is particularly preferred for providing larger portions of a dental restoration due to the relatively high mechanical stability of the zirconia in use of the dental restoration in a patient's mouth.

Generally for the purpose of this specification a material a dental restoration is made of should not be detrimental to the patient's health and thus free of hazardous and toxic components being able to migrate out of the restoration. Dental restorations are typically of small size and may comprise sections having a wall thickness in the range of about 100 µm to about 2000 µm, or in the range of about 100 µm to about 500 µm. The total volume of a dental restoration is typically below about 100 ml or below about 50 ml or below about 10 ml or below about 5 ml.

In one embodiment the method comprises steps of successively providing layers of particles. Preferably layers of particles are provided by the automated build-up technique, further details of which are described in the examples below. During such layering at least one color is dispensed on selected layers before a subsequent layer is provided. Further a plurality colors may be dispensed on selected layers before a subsequent layer is provided. The color or colors may be dispensed in a two-dimensional pattern. The layers of particles each may be colored over a generally contiguous area which is independent from a dimension of the dental restoration.

In one embodiment a liquid is dispensed on selected layers before a subsequent layer is provided. Further a plurality of differently colored liquids may be dispensed on selected layers before a subsequent layer is provided. Each liquid may comprise a color, for example in the form of a colorant or coloring solution (for example as described in EP-A-1 486 476), and the plurality of liquids may comprise different colors. Thus the dispensation of the liquid(s) may also provide for the dispensation of the color(s). The liquid may be generally adapted for penetrating the powder so that a plurality of particles within the powder can take on the color. A majority or substantially all of the liquid may be removed after the coloring, for example by drying.

Accordingly a dental blank precursor is preferably obtained which is formed by a bulk of generally loosely accumulated particles. The particles preferably leave spaces between and thus the dental blank precursor is open-celled (also sometimes referred to as porous). Such an open-celled dental blank precursor typically has outer boundaries defining an initial volume. The density of the dental blank precursor based on this initial volume is typically lower than the density of the particles the dental blank precursor is made of. Such density of the dental blank precursor is further referred to herein as "initial density". The initial density further preferably refers to a density of a dried open-celled dental blank precursor. This means a dental blank precursor from which excess liquid is removed.

In one embodiment the method comprises the step of compressing the dental blank precursor to obtain the dental blank and thereby to increase the initial density to an intermediate density. Accordingly the dental blank preferably has the intermediate density. Further the compressing preferably is performed at a pressure which causes the particles to adhere with one another. Thus the dental blank may be provided with a dimensional stability which enables handling in one piece. This means that the intermediate density of the dental blank preferably is still lower than the density of the particles the blank is made of. However the intermediate density is preferably higher than the initial density, although the blank preferably still has an open-celled structure at that intermediate density.

In one embodiment the method comprises the step of providing means for compressing the dental blank precursor. Preferably the dental blank precursor is compressed into a shape that is independent from the tooth shape or dental restoration shape information. The dental blank precursor may be uniaxially compressed. Thereby the dental blank precursor is preferably provided in a cavity or a frame (preferably closed at the bottom to prevent particles from flowing out) and compressed between two dies urged against each other from opposing sides, for example. The skilled person will recognize that only one die may be used for pressing the dental blank precursor in a cup shaped cavity. Further the dental blank precursor may be compressed by uniaxially pre-pressing and subsequent isostatic recompression. Isostatic recompression may for example provide the dental blank with a maximized uniform structure. For isostatic recompression the (uniaxially pre-pressed) dental blank may be provided in a liquid within a flexible bag and the liquid may be pressurized to hydraulically recompress the pre-pressed dental blank. The so formed dental blank preferably has a sufficient mechanical stability such that it can be handled and machined, for example ground or milled.

In one embodiment the method comprises the steps of providing the dental blank precursor in a build up chamber and compressing the dental blank precursor within the build-up chamber. Such a build-up chamber may for example be provided in a cartridge which is alternatively removably placeable in a build-up device and removably placeable in a press for compressing the dental blank precursor. Such a cartridge is described in more detail in the examples.

In one embodiment the method comprises the step of pre-sintering the dental blank to form a pre-sintered dental blank. Thereby the dental blank may be exposed to a temperature of between 500° C. and 1100° C. (depending, inter alia, on the material the dental restoration precursor is made of). The pre-sintering step is preferably performed at a temperature and duration such that the obtained dental blank is open-celled or partially open and closed celled and has a pre-final density which is higher than the intermediate density. The step of pre-sintering preferably provides for properties of the pre-sintered dental blank which allows machining and may particularly prevent uncontrolled chipping during machining. Further the mechanical stability of the pre-sintered dental blank is preferably higher than the mechanical stability of the dental blank (sometimes also referred to as "green" dental blank in the dental field). Thus the pre-sintered dental blank is preferably relatively robust relative to mechanical stress during handling and/or machining.

The person skilled in the art will recognize that the pre-sintering step is optional and that the (green) dental blank may be used directly for machining the dental restoration therefrom, although this is not preferred.

In a further embodiment the method further comprises the step of removing a portion of the dental blank or pre-sintered dental blank to obtain a dental restoration precursor. The blank may be machined, for example milled or ground, to remove a portion of the blank. This may be performed in a computer controlled milling or grinding machine based on the dental restoration shape information. The dental restoration precursor may correspond in shape to a three-dimensionally proportionally scaled (in particular enlarged) shape of the finished dental restoration.

In a further embodiment the method further comprises the step of sintering the dental restoration precursor. Thereby the dental restoration precursor is preferably exposed to a temperature of between 800° C. and 1600° C. (depending, inter alia, on the material the dental restoration precursor is made of). Sintering preferably causes the dental restoration precursor to further increase in density (and accordingly to three-dimensionally shrink in shape for which reason the dental restoration precursor is provided at a three-dimensionally enlarged shape). The final density of the dental restoration preferably corresponds generally to the density of the particles from which the blank was made. In other words the dental restoration is preferably free of open cells and voids, and the final density is higher than the initial density, the intermediate density and the pre-final density as mentioned above.

In one embodiment the method comprises the step of veneering the dental restoration. Although the step is optional, because the method of the invention preferably may provide an optically pleasant dental restoration made of ceramic only, such a step is not excluded and may be used as appropriate. The veneering may comprise providing a glass ceramic veneer, for example. However the person skilled in the art will be aware of alternative veneering techniques, like for example manual layering of materials which are subsequently fired for hardening or which harden chemically. The manual layering may further include the use of dental paints and/or effect shades. The method may further comprise the step of glazing the dental restoration. Thus a dental restoration may be obtained having good aesthetic and mechanical properties.

In a further aspect the invention relates to a system for making a customized dental blank. The system comprises:
  a data interface for receiving individual tooth color information, for example associated with a particular patient or a tooth of a patient;
  a build-up device comprising:
    a reservoir for holding particles;
    a build-up receptacle adapted for successively receiving portions of the particles layered on top of each other to form a dental blank precursor;
    a color dispensing unit which is adapted for dispensing at least one color on selected particle layers in a two-dimensional pattern, wherein the layers are selected and/or the two dimensional patterns are determined based on the individual tooth color information;
  and a press which is adapted for compressing the dental blank precursor to form the dental blank; and
  the system being adapted to perform the method according to any of the preceding claims.

In one embodiment the build-up chamber is removable from the build-up device and receivable in the press. The press may comprise a pressing die for uniaxially compressing the dental blank precursor within the build-up receptacle. The build-up receptacle may be adapted for holding the dental blank precursor, in particular during compression by the press. Further the pressing die may be sized and shaped such that it is movable into the build-up chamber.

In a further embodiment the system comprises two pressing dies. The build-up chamber may be formed by a through-hole through a cartridge. Preferably the two pressing dies are adapted for a movement into the build-up chamber (or the through-hole) from opposite sides.

In an alternative embodiment the system may further comprise a press which has a liquid for hydraulically or isostatic recompressing a uniaxially pre-pressed dental blank.

In a further aspect the invention relates to a customized dental blank having an open-celled material structure provided by adherent particles, wherein the blank is colored according to individual tooth color information. The customized dental blank is preferably obtained by the method of the invention.

DETAILED DESCRIPTION OF THE INVENTION

Figure 1:
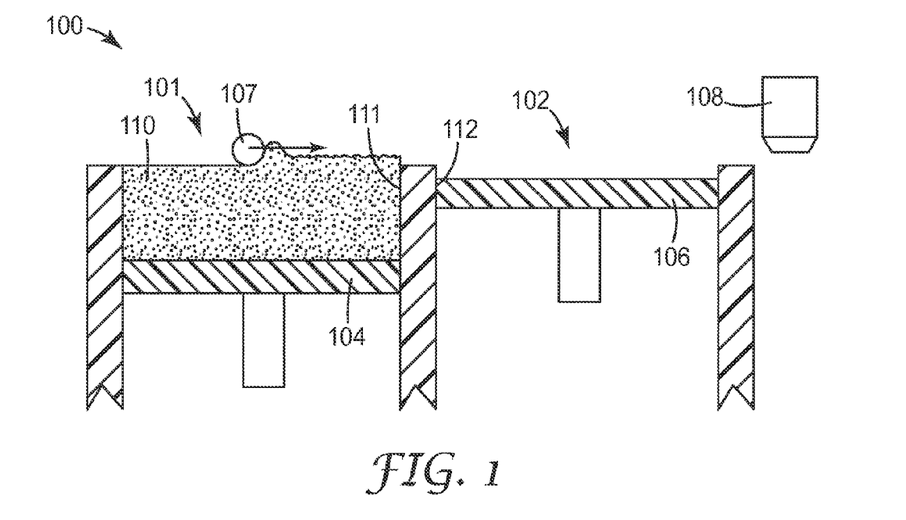
FIG. 1 is a schematic illustration of a rapid prototyping device as it may be used with the present invention.

FIG. 1 is a schematic illustration of a rapid prototyping device 100 (also sometimes referred to as "3D printer") as it may be used with the present invention. The device 100 is generally adapted to build up a three-dimensional object based on digital data which represent a shape of that object. In particular the device 100 is adapted to build up a mechanically stable three-dimensional object (although preferably otherwise used according to the present invention) from a particles provided as a powder and a liquid locally added to the powder. Such a device is for example available under the designation ZPrinter™ 310 plus from the company ZCorp.

The device 100 of the example has a reservoir chamber 101 and a so-called build-up chamber 102. In the example illustrated the build-up chamber 102 is empty and prepared for receiving an initial amount of the powder supplied from the reservoir chamber 101. A recoater 107 is used for transferring powder from the reservoir chamber 101 toward the build-up chamber 102. Lifts 104, 106 of the reservoir chamber 101 and the build-up chamber 102, respectively, provide for controlling the powder level within the respective chamber 101/102. In particular the build-up chamber lift 106 is positioned offset from an upper opening 112 of the build-up chamber 102 and thus leaves a defined space which can be filled by powder to form an initial powder layer within the build-up chamber 102. The reservoir chamber lift 104 on the other hand is positioned to provide a determined portion of powder above an opening 111 of the reservoir chamber 101. The powder portion above the reservoir opening 111 may for example generally correspond to the space left within the build-up chamber 102. The lifts 104, 106 may be position stepwise for providing powder from the reservoir chamber 101 into the build-up chamber 102 in the form of multiple layers.

Further the device 100 has a dispensing unit 108 for selectively providing a liquid onto the exposed or uppermost powder layer in the build-up chamber 102. The liquid is preferably selected such that a portion of the powder is penetrated so that a color contained in the liquid colors the penetrated portion. The dispensing unit 108 is movable in at least two dimensions (in the Figure between the left and right and in a dimension perpendicular to the plane of the Figure) and may be positioned at defined positions over at least the build-up chamber 102. In operation of the device 100 a layer of powder may be provided in the build-up chamber 102 and liquid may be dispensed on a part or the entire surface of that layer before the next powder layer is provided. On that next layer again liquid may be dispensed on a part or the entire surface of that layer before a further powder layer is provided. Preferably the position of the dispensing is controlled to create colored portions on top of each other in adjacent layers to form larger colored portions. The steps of providing a layer and dispensing liquid may be repeated until a contiguous colored portion of a desired size and shape is reached.

Figure 2:
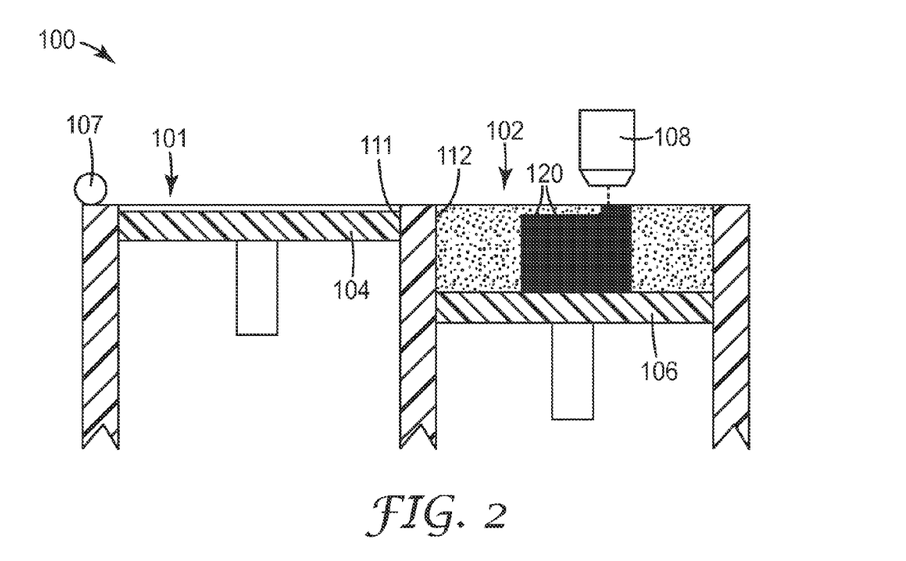
FIG. 2 is a schematic illustration of the rapid prototyping device shown in FIG. 1.

FIG. 2 shows the same device 100 as shown in FIG. 1 at a different stage of operation. In the example a colored portion 120 is built up in the build-up chamber 102. The shape of the build-up chamber 102 generally provides the shape of a dental blank precursor. In the example shown the dental blank precursor comprises the colored portion 120 and further a generally non-colored portion outside the colored portion 120. This is to illustrate the capability of the device to selectively color portions of the powder. However (although not shown) preferably the entire amount of powder in the build-up chamber is colored. The build-up chamber and thus also the dental blank precursor have a general uniform cross-section across a multiplicity of powder layers. The cross-section may be generally rectangular or generally round, for example square shaped or circular. Although the colored portion 120 forms a contiguous area the dental blank precursor overall preferably has an open-celled structure at least after drying the liquid dispensed on the powder. Further the powder is preferably loose also in the colored portion 120. The size and shape of the dental blank precursor is preferably predetermined and independent from the particular shape of the dental restoration obtainable or obtained from that dental blank precursor. However the dental blank precursor may be colored according to individual tooth color information associated. Thus a dental blank precursor is formed which has a standardized shape but customized coloring.

To provide such coloring the dispensing device preferably is adapted to dispense several liquids of different colors. For example on each layer of a multiplicity of layers for forming a dental blank precursor, a two-dimensional image may be printed by dispensing one liquid of a certain color or more liquids of different colors. It is noted that although the image as such is two-dimensional the liquid(s) forming the image preferably saturate the powder in an additional dimension. Accordingly a three-dimensional portion (preferably at least one powder layer thick) of saturated powder is obtained through which the image continues. The image may correspond in outer shape to the cross-section of the dental blank precursor and may be contiguous. Further the image may comprise one or more colors which are printed in a pattern based on individual tooth color information. Thus a multiplicity of individually colored images are layered on top of each other and provide the dental blank precursor with customized coloring. Such a customized coloring may for example form a color gradient in one or more dimensions within the dental blank precursor so that a dental restoration formed from that dental blank precursor obtains a color gradient which resembles that of a natural tooth.

The individual tooth color information may be obtained from a computer in which a three-dimensional model of a dental restoration for a particular patient is stored. The three-dimensional model preferably comprises information about the shape and the color of the dental restoration. In particular the model of the dental restoration may comprise information about color at a particular position within the three-dimensional model. Preferably in more particular the model of the dental restoration may comprise corresponding color information for a multiplicity of positions within the three-dimensional model.

The tooth color information may in one example be obtained from defining a first color at a first position and a second color at a second position within the three-dimension dental restoration model, and automatically assigning further colors at positions between the first and second position. Such further colors may for example be automatically calculated according to a linear gradient based on the first and second colors. The first and second color may be entered manually by a user, for example in the form of tooth color codes obtained from a standard tooth color scheme. A known tooth color scheme is for example the VITA 3D™ Master shade guide. The three-dimensional dental restoration model may be automatically analyzed, for example virtually sliced in layers, to obtain a multiplicity of patterns according to which the liquid is printed on powder layers.

Figure 3:
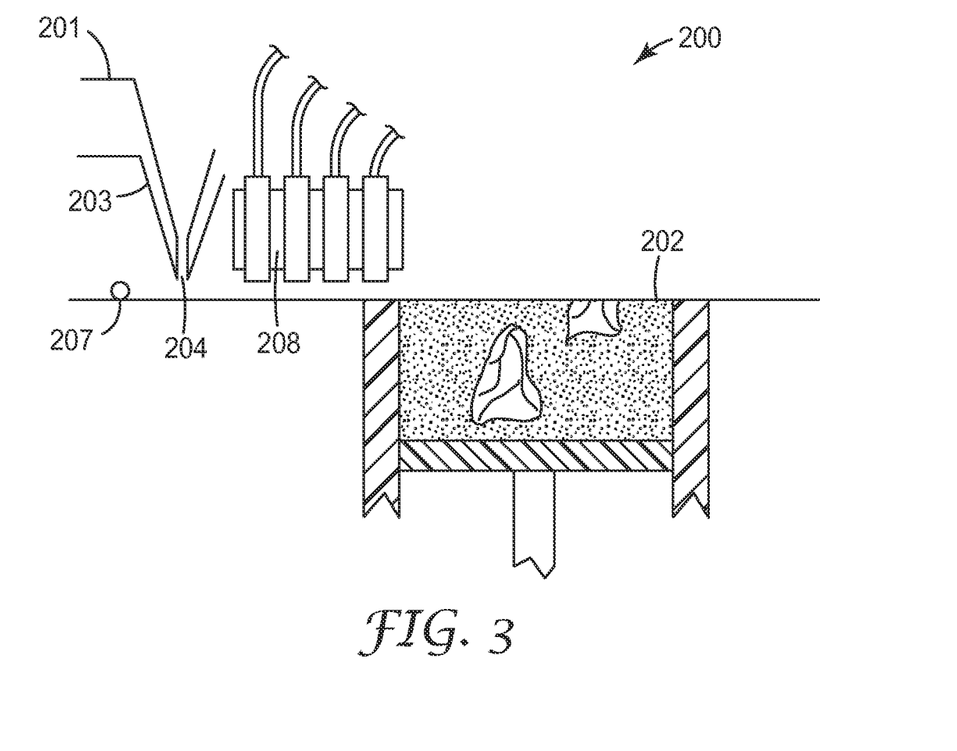
FIG. 3 is a schematic illustration of an alternative rapid prototyping device as it may be used with the present invention.

FIG. 3 shows a device 200 having a print head 208 for dispensing four different colors. The device corresponds in function generally to the device described above, however with a differently configured reservoir chamber 201. The reservoir chamber 201 in this example is movable relative to the build-up chamber 202 so as to dispense the powder directly from the reservoir chamber 201 into the build-up chamber 202. In the example the reservoir chamber 201 has a tube 203 which is closed by a lower dispensing nozzle 204. The tube 203 in the Figure is filled with powder which is releasable from the tube through the dispensing nozzle 204. For dispensing the reservoir chamber 201 can be positioned over the opening of the build-up chamber 202, powder is released into the build-up chamber and the reservoir chamber 201 can be moved sideways to wipe the dispensed powder generally planar. The device 200 in the example for this purpose has a recoater 207 which may be attached to the movable reservoir chamber 201. In this way a multiplicity of layers can be provided into the build-up chamber. After each deposition of a powder layer into the build-up chamber the print head 208 may be moved over the last deposited layer for printing an image based on individual tooth color information as described above. The print head 208 in the example is suspended on a support (not shown) which provides for motor driven and dimensionally controlled positioning of the print head 208 in at least two dimensions. Further the print head in the example comprises an ink-jet nozzle for each color. The ink-jet nozzles and the support can be computer controlled for printing the image. The build-up chamber 202 holds an amount of powder which is individually colored. In the example the coloring of individual teeth is illustrated although the illustrated boundaries doe not correspond to boundaries of the dental blank precursor.

Figure 4:
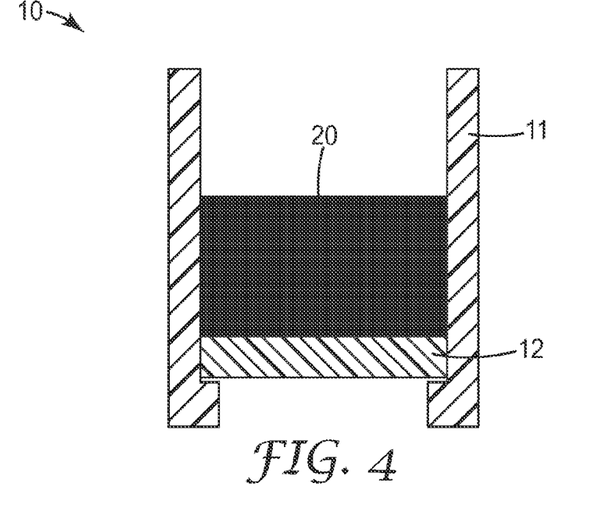
FIG. 4 is a cross-sectional view of a cartridge containing a blank precursor obtained from a build-up process according an embodiment of the invention.

FIG. 4 shows a cartridge 10 which preferably forms at least part of a build-up chamber. Although not shown the devices shown in FIGS. 1 to 3 may make use of such a cartridge 10. The cartridge 10 is preferably removably placeable in a rapid prototyping device as described. The dental blank precursor 20 is shown in the cartridge 10. The dental blank precursor 20, which is preferably formed of loose powder, rests on a tray 12 which is movably arranged within the cartridge housing 11. The tray 12 preferably facilitates positioning and handling of the powder during build-up. Further the tray 12 prevents the powdery dental blank precursor from flowing out of the cartridge during a transfer of the cartridge 10 form the build-up device to a press (not shown). At the stage illustrated the dental blank precursor 20 may be compressed within the cartridge 10 and removed from the cartridge 10 after.

Figure 5:
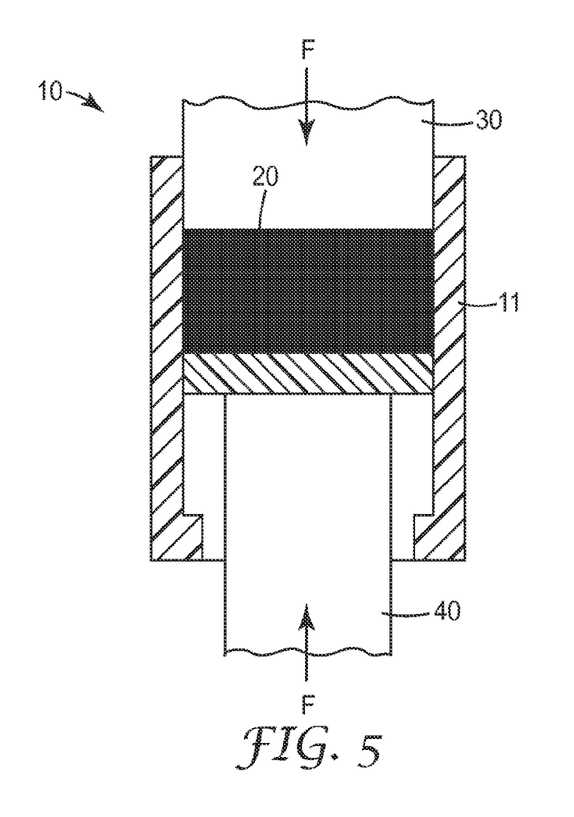
FIG. 5 is a cross-sectional view illustrating compression of a blank precursor according an embodiment of the invention.

FIG. 5 illustrates uniaxial compression of the dental blank precursor 20 in the cartridge 10 to form the dental blank. An upper compression die 30 and a lower compression die 40 are positioned within the cartridge housing 11 with the dental blank precursor 20 placed between. For compressing the dental blank precursor 20 the upper compression die 30 and the lower compression die 40 are urged toward another. The force F at which the compression dies 30, 40 are urged toward another is preferably selected to cause a pressure on the dental blank precursor within a range of about 10 MPa and 1000 MPa, in more particular between about 30 MPa and 150 MPa. At such pressures the powder particles typically tend to adhere to one another.

The invention claimed is:

1. A method of making a customized dental blank comprising:
   providing individual tooth color information associated with one or more teeth of a patient;
   forming an open-celled dental blank precursor by successively providing layers of particles where each layer is provided with at least one color before a subsequent layer is provided, wherein the at least one color is provided in accordance with the individual tooth color information;
   providing individual dental restoration shape information associated with the patient;
   providing the dental blank precursor with a shape that is independent from the dental restoration shape; and
   compressing the dental blank precursor to provide the dental blank.

2. The method of claim 1, wherein the particles comprise or essentially consist of ceramic material.

3. The method of claim 2, wherein the ceramic material comprises or essentially consists of zirconia.

4. The method of claim 1, in which a plurality of colors is dispensed on selected layers before a subsequent layer is provided.

5. The method of claim 1 in which the color(s) is/are dispensed in a two-dimensional pattern or area.

6. The method of claim 1 further comprising optionally pre-sintering the dental blank and removing a portion of the dental blank or pre-sintered dental blank to obtain a dental restoration precursor.

7. The method of claim 6, further comprising the step of sintering the dental restoration precursor.

8. The method of claim 1, wherein the customized dental blank is customized in color but standardized in shape.

9. The method of claim 1, wherein the step of providing the dental blank precursor with a shape that is independent from the dental restoration shape comprises removing material from the dental blank precursor.

10. A system for making a customized dental blank, comprising:
 a data interface for receiving individual tooth color information;
 a build-up device comprising:
  a reservoir for holding particles;
  a build-up chamber adapted for successively receiving portions of the particles layered on top of each other to form an open-celled dental blank precursor;
  a color dispensing unit which is adapted for dispensing at least one color on selected particle layers in a two-dimensional pattern, wherein the layers are selected and/or the two dimensional patterns are determined based on the individual tooth color information;
  and a press which is adapted for compressing the dental blank precursor to form the dental blank;
 the system being adapted to perform the method of claim 1; and
 wherein the build-up chamber is removable from the build-up device and receivable in the press, and wherein the press further comprising a pressing die for uniaxially compressing the dental blank precursor within the build-up receptacle.

11. The system of claim 10, wherein the build-up chamber is formed by a through-hole through a cartridge.

12. The system of claim 11, comprising two pressing dies, wherein the two pressing dies are adapted for a movement into the build-up chamber from opposite sides.

13. A customized dental blank having an open-celled material structure provided by adherent particles, wherein the blank is colored according to individual tooth color information associated with one or more teeth of a patient by successively providing layers of particles where each layer is provided with at least one color before a subsequent layer is provided, wherein the at least one color is provided in accordance with the individual tooth color information associated with one or more teeth of the patient and wherein the blank is shaped independent from individual dental restoration shape information associated with the patient.

14. The customized dental blank according to claim 13, wherein the blank is colored dependent on individual dental restoration information associated with the patient.

* * * * *

UNITED STATES PATENT AND TRADEMARK OFFICE
CERTIFICATE OF CORRECTION

PATENT NO. : 10,182,892 B2
APPLICATION NO. : 14/404038
DATED : January 22, 2019
INVENTOR(S) : Malte Korten Page 1 of 1

It is certified that error appears in the above-identified patent and that said Letters Patent is hereby corrected as shown below:

In the Specification

Column 12
Line 2, delete "doe" and insert -- does --, therefor.

In the Claims

Column 12
Line 58, in Claim 5, delete "claim 1" and insert -- claim 1, --, therefor.

Column 12
Line 60, in Claim 6, delete "claim 1" and insert -- claim 1, --, therefor.

Signed and Sealed this
Twenty-second Day of October, 2019

Andrei Iancu
*Director of the United States Patent and Trademark Office*